United States Patent [19]

Magro

[11] Patent Number: 4,976,681
[45] Date of Patent: Dec. 11, 1990

[54] PACER INTERFACE DEVICE

[75] Inventor: Alfred E. Magro, Woburn, Mass.

[73] Assignee: Aries Medical, Inc., Woburn, Mass.

[21] Appl. No.: 187,053

[22] Filed: Apr. 27, 1988

[51] Int. Cl.$^5$ ............................................ A61N 1/365
[52] U.S. Cl. .................................... 600/17; 128/419 P
[58] Field of Search .................... 128/709, 419 P;710, 128/696; 600/16, 17, 18

[56] References Cited

U.S. PATENT DOCUMENTS

| Re. 32,361 | 2/1987 | Duggan | 128/696 |
| 3,554,198 | 1/1971 | Tatoian et al. | 128/419 P |
| 3,742,947 | 7/1973 | Hashem | 128/696 |
| 3,750,644 | 8/1973 | Ragsdale | 600/17 |
| 4,027,663 | 6/1977 | Fischler et al. | 128/710 |
| 4,080,958 | 3/1978 | Bregman et al. | 600/16 |
| 4,204,524 | 5/1980 | Martin et al. | 600/17 |
| 4,307,725 | 12/1981 | Sowton et al. | 128/419 PG |
| 4,601,291 | 7/1986 | Boute et al. | 128/710 |
| 4,674,509 | 6/1987 | Decote, Jr. | 128/419 PT |
| 4,742,831 | 5/1988 | Silvian | 128/710 |
| 4,787,368 | 11/1988 | Kageyama | 600/18 |
| 4,803,996 | 2/1989 | Peel et al. | 128/710 |
| 4,827,906 | 5/1989 | Robicsek et al. | 60/17 |

OTHER PUBLICATIONS

"Failure of Intraaortic Balloon Counterpulsation Caused by Pacing or Other Electrical Artifacts: A New Method of Correction", F. Robicsek, et al., published in the *Journal of Cardiac Surgery* 2:407–410, Sep., 1987.

Primary Examiner—Lee S. Cohen
Assistant Examiner—Kennedy J. Schaetzle
Attorney, Agent, or Firm—Robert M. Asher

[57] ABSTRACT

A method and device for providing a timing signal to a medical device in response to light emitting indicators on a cardiac pacer. The device is optically coupled to the light emitting indicators, but is electrically isolated from the cardiac pacer. A timing signal is generated in response to activation of the light emitting indicators which indicate that an R wave was sensed or a ventricular pace signal was sent.

8 Claims, 2 Drawing Sheets

PACER INTERFACE DEVICE

BACKGROUND OF THE INVENTION

The present invention relates to a method of controlling the timing in medical equipment, in particular, a method for using a cardiac pacer to control the timing of an intraaortic balloon pump.

When a patient undergoes surgery, it is a common practice in surgery to use an electrocautery device for cutting through the skin and for cauterizing the skin about the opening to prevent or to minimize bleeding. Other electrosurgery devices are also in common use. When such a device is used, electrical interference with the ECG is caused. The electrosurgery device generates voltages in the hundreds and thousands of volts at radio frequencies and at other frequencies as well, often including the same frequency components as the ECG. Thus, electronic filters alone cannot separate out these interfering signals.

A number of devices in the medical laboratory rely upon the electrocardiogram (ECG) to control their timing. Therefore, difficulties arise when electrical interference causes the loss of the electrocardiogram signal. A particular case in point is the heart patient who has an intraaortic balloon pump to assist in the pumping action of his heart. The intraaortic balloon pump generally uses the R wave of the electrocardiogram signal to synchronize the timing of the intraaortic balloon pump. Thus, a patient relying upon an intraaortic balloon pump has often been placed at risk when an electrosurgery device obscures the ECG. The timing of the intraaortic balloon pump can then no longer rely on the R wave in the ECG.

It is an object of the present invention to coordinate the timing of an intraaortic balloon pump with the pumping of a patient's heart without relying upon the electrocardiogram.

SUMMARY OF THE INVENTION

The present invention is directed to a method in which an electronic cardiac pacer is used to pace a patient's heart. Control of a medical device, such as an intraaortic balloon pump, is electronically coupled to the electronic cardiac pacer. The triggering of the intraaortic balloon control system is made in response to a pace signal or an R sense signal from the pacer. In accordance with the present invention, the intraaortic balloon control system is optically coupled to the cardiac pacer so as not to cause any feedback or interference with the pacer.

The device of the present invention is an interface between the cardiac pacer and an intraaortic balloon pump control system. The interface includes photoresponsive devices such as phototransistors for receiving light signals from light emitting diodes (LED's) on a cardiac pacer. The device further includes means for coupling these signals to the intraaortic balloon control system so that the triggering of the balloon pump can be made in response to a pace signal or an R sense signal. Since a cardiac pacer attaches directly to the heart, its timing is not affected by the use of electrosurgery devices, the timing of the intraaortic balloon pump is independent of those devices when the interface device is used. Since the signals given off by the pacer indicate the timing of the patient's heart, they may be used as substitutes for the R wave from the electrocardiogram.

Other objects and advantages of the present invention will become apparent from the following description taken in conjunction with the drawings.

DETAILED DESCRIPTION OF THE PREFERRED EMBODIMENT

The present invention is directed to timing a medical device by using a cardiac pacer instead of an electrocardiogram. If a patient does not have an electronic cardiac pacer, the same effect can be obtained by inserting a Swan pacing catheter to temporarily connect a cardiac pacer to the heart. Cardiac pacers generally are provided with light emitting diodes (LED's) which signal the operation of the pacer and also provide an indication of the R wave signal from the heart when it is detectable. For example, a Medtronic Model 5330AV Sequential Demand Pulse Generator includes three LED's placed horizontally across the top of the pacer. These LED's are provided to indicate the atrial pace pulse, a ventricular pace pulse and a ventricular sense indicator. In accordance with the present invention, rather than attempting to sense the R wave from the electrocardiogram directly, the LED's on a cardiac pacer are used to provide an equivalent signal. Either the R wave is sensed by the cardiac pacer and that LED will light, or if the heart is not pacing itself, the ventricular pace signal can be used as the timing trigger instead of the R wave signal. It may also be possible to trigger off of the atrial pace signal, but the present embodiment preferably relies on the ventricular pace and R sense signals, making no use of the atrial pace signal.

In an intraaortic balloon control system, the inflation and deflation of the intraaortic balloon is normally adjusted to occur a preset time following the occurrence of an R wave signal in an electrocardiogram. The adjustment of the preset time is made in accordance with a reading of the patient's arterial pressure. Instead of using the electrocardiogram to provide the trigger signal, in accordance with the present invention, an optical connection is made with the LED's of a cardiac pacer to trigger the control system in response to an R sense signal, as usual, or the ventricular pace signal when the R sense signal is not available. Thus, inflation and deflation will occur an adjusted preset time following a timing signal representing either the R sense or ventricular pace signal.

Figure 1:
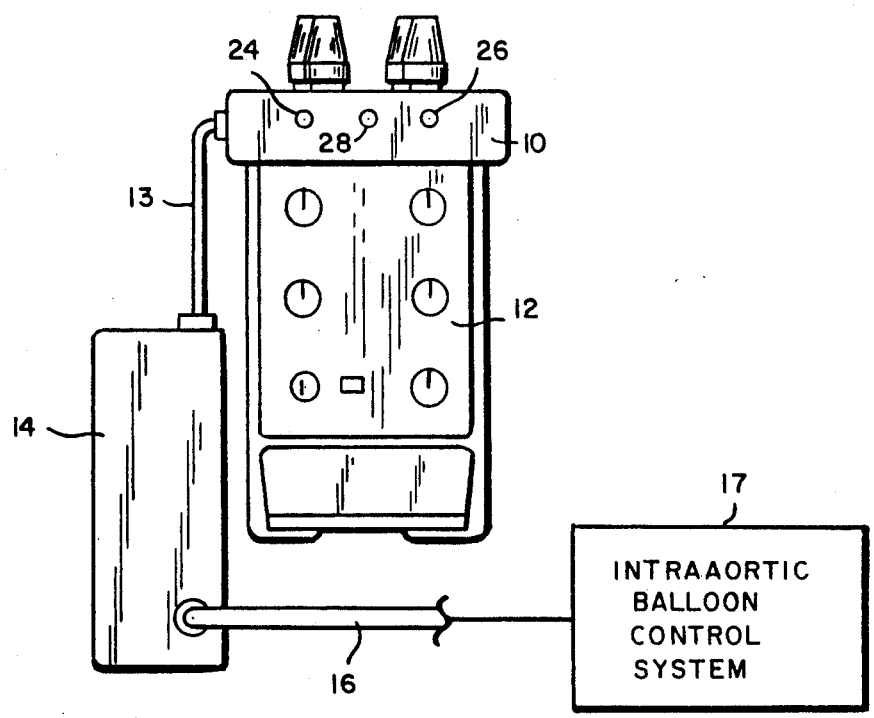
FIG. 1 shows the pacer interface device of the present invention attached to a cardiac pacer.

Referring now to FIG. 1, the interface device of the present invention is shown. A plastic light shield 10 is provided for attachment to a cardiac pacer 12. The shield 10 clips over the pacer 12 where the three LED's are located. The plastic shield 10 can be made to snap into place over the cardiac pacer or may be clamped onto the pacer in any conventional manner. It is important that when the shield 10 is attached to the pacer 12 that the LED's are properly aligned with the photoresponsive devices on the inside of the interface device. The plastic shield 10 is provided with its own three LED's so that these signals are still visible even when the shield is in place. The shield 10 should prevent external light from reaching the phototransistors so that they are solely responsive to the LED's of the electronic pacer 12.

An output line 13 extends from the plastic shield 10 and provides electrical connections to the photoresponsive devices in this shield so as to output the signals to an electronic control portion 14 of the interface. The electronics 14 may be located as shown in FIG. 1 or located within the plastic shield 10. An output line 16 from the control portion 14 provides the trigger signal to the intraaortic balloon control system 17. Lines 13 and 16 should be properly shielded so as not to be adversely affected by RF electrical interference from the electrosurgery devices. A further precaution against the RF interference is taken by including electrical filters in the electronics.

Figure 2:
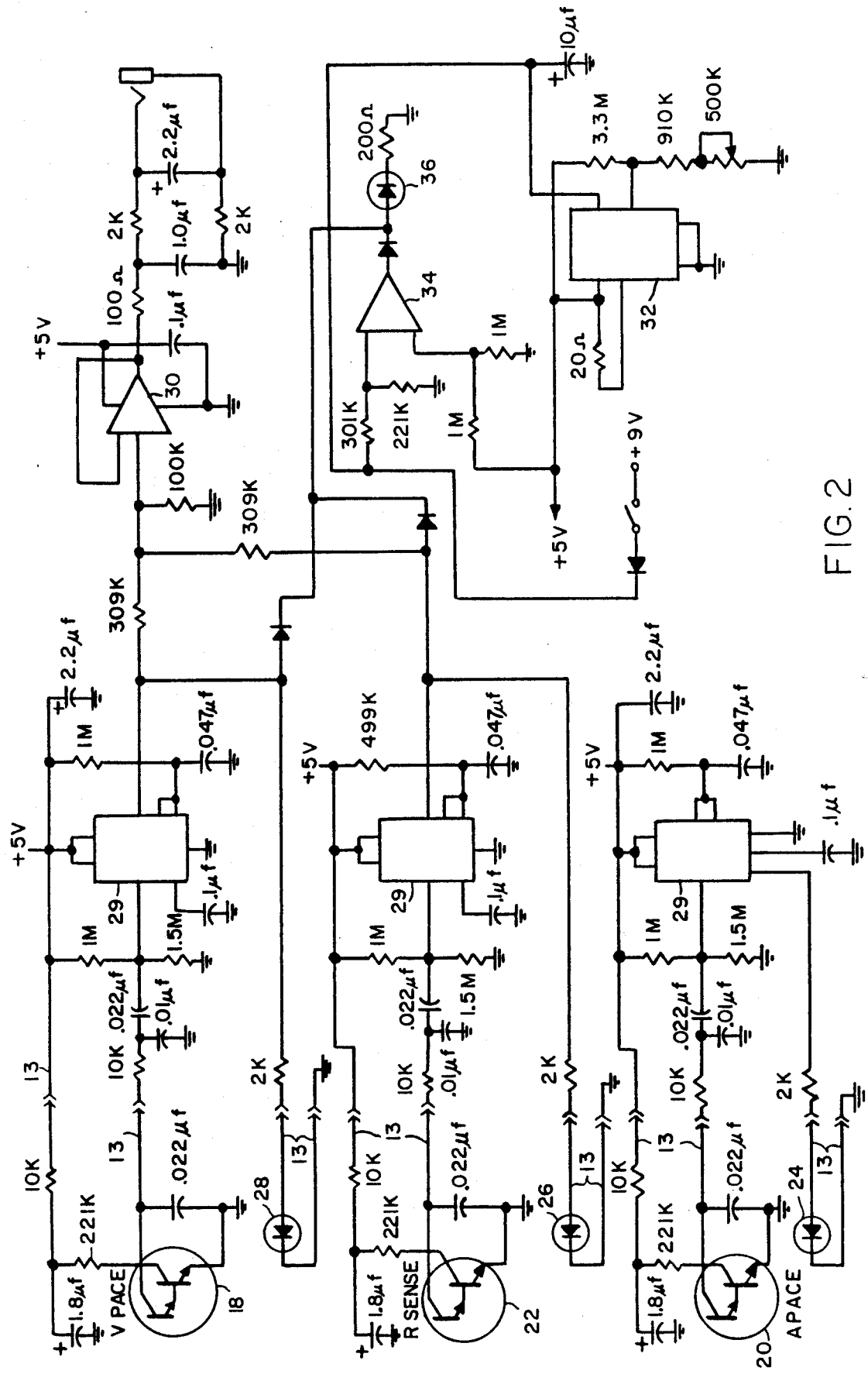
FIG. 2 is an electrical schematic of the pacer interface device of the present invention.

The electronics of the interface device are shown in greater detail in FIG. 2. The ventricular pace signal is sensed by a phototransistor 18. The arterial pace signal is sensed by a phototransistor 20 and the R sense signal is sensed by a phototransistor 22. These phototransistors are positioned within the shield 10 so that they are optically coupled to their respective LED on the pacer. An electronic channel is provided for each of the phototransistors. Each phototransistor is provided with a connection to the 5 volt source voltage. Filters are formed at the input end of the interface by a 0.022 microfarad and 0.01 microfarad capacitor and a 10K resistor which are connected between the line 13 and ground. These components filter out stray RF radiation in a manner which is well known in the electronics art. The arterial pace signal is not used for triggering by the intraaortic balloon control system 17, therefore no use is made of the arterial pace signal other than to connect it to an LED 24 on the exterior of the plastic shield 10. Therefore, the electronic channel associated with the phototransistor 20 merely causes an LED 24 to light in response to the lighting of the corresponding LED on the cardiac pacer.

The R sense signal and the ventricular pace signal are used interchangeably. When the heart is pacing itself, it will be providing an R wave which is sensed by the cardiac pacer and is indicated by the R sense LED on the pacer. When the heart is unable to pace itself, the pacer will be operating and it is the ventricular pace signal which is used by the intraaortic balloon control system 17 as a triggering signal. Each of these signals is indicated by a corresponding LED on the exterior of the plastic shield 10 so that the LED signals are not lost as a result of the use of the interface device. When the R sense signal lights, the phototransistor 22 causes LED 26 to light up. When the phototransistor 18 senses light from the ventricular pace signal LED, LED 28 on the interface is caused to light up.

The phototransistors normally output a high signal. When light is sensed from the pacer, a phototransistor will conduct thereby outputting a low pulse. This is provided to an inverting one shot 29. In the presently preferred embodiment, the one shot 29 in the ventricular pace and R sense channel is an ICM7556 and in the arterial pace channel an ICM7555 is used. In response to a low pulse, the one shot 29 will output a high signal. In the atrial pace channel this only serves to light up LED 24. In the ventricular pace channel, a high output from one shot 29 accomplishes a number of functions. It lights LED 28, and battery indicator LED 36 momentarily and is fed into a driver 30. Likewise in the R sense channel, a high output from the one shot 29 flashes its respective LED 26, and battery indicator LED 36 and is fed into the driver 30. Thus when either the ventricular pace signal or the R sense signal is lit, the driver 30 will be activated. Thus, either one of these signals will cause the driver to send a timing pulse through the output cable to the intraaortic balloon control system. Filters are provided going into the ouput cable 16 to filter out the RF inferference from an electrosurgery device as was done for the input line. It should be noted that the interface device of the present invention is completely electronically isolated from the electronic cardiac pacer. Any malfunction in the interface device or the control system cannot be electronically fed back into the cardiac pacer. Thus, the operation of the pacer will not be affected by the use of the interface device.

The device in FIG. 2 is powered by a 9 volt battery. A 5 volt regulator circuit 32 is provided for regulating the 9 volts so as to provide a 5 volt power source to the phototransistor channels. The presently preferred regulator is an ICL 7663. Also, a differential amplifier 34 is provided for comparing a fraction of the 9 volt input with a fraction of the regulated 5 volt supply. The fractions are set by voltage dividers so that the amplifier 34 causes the battery LED indicator 36 to light when the battery falls below a threshold such as 6 volts. When the battery is above the threshold, indicator 36 flashes when either a ventricular pace or R sense signal is received. Should the battery get low, the LED 36 will remain on and the user will recognize that a new battery is needed.

The present invention avoids the problems normally caused by electrical interference from electrosurgery devices. The timing provided by an electronic cardiac pacer may be used to control the triggering of the intraaortic balloon control system. Furthermore, by picking up the signals from the pacer optically, the interference is electrically isolated from the pacer thereby eliminating the danger of electrically interfering with the cardiac pacer.

Changes and modifications to the embodiment described above will be apparent to those skilled in the art. For example, one may choose to use the arterial pace signal through the interface as a trigger. The interface may be used with devices other than the intraaortic balloon which also need a trigger signal from the heart. These and other changes can be made without departing from the spirit and the scope of the invention and without diminishing its attendant advantages. It is therefore intended that such changes and modifications be covered by the following claims.

I claim:

1. An interface device comprising:
   means, electrically isolated from an electronic cardiac pacer, for receiving pace signals and R wave sense signals from said cardiac pacer; and
   means for providing an electrical timing signal in response to receipt of either one of said pace signals or one of said R wave sense signals by said receiving means.

2. The device of claim 1 wherein said receiving means comprises a photoresponsive device.

3. The device of claim 2 wherein said photoresponsive device is a phototransistor.

4. The device of claim 1 wherein said receiving means comprises means for optically sensing a pace signal or an R wave sense signal.

5. The device of claim 1 further comprising means for attaching said receiving means to said cardiac pacer and for preventing external light from impinging on said receiving means.

6. The device of claim 1 further comprising battery means for providing power to operative said device.

7. The device of claim 6 further comprising means for detecting when said battery means is low on power and means for signalling in response to said low power condition.

8. An interface device comprising:
an opaque shield attachable over a plurality of light emitting indicators on an electronic cardiac pacer;
a plurality of photoresponsive devices located within said shield so that each photoresponsive device is optically coupled with one of said light emitting indicators when said shield is attached to said cardiac pacer;
a plurality of light emitting diodes located on said shield so as to be visible when said shield is attached to said cardiac pacer and means for activating one of said light emitting diodes when a corresponding light emitting indicator is lit;
means for driving an electrical timing signal in response to a signal from one of said photoresponsive devices; and
means for providing said electrical timing signal to an intraaortic balloon pump control system.

* * * * *